United States Patent [19]

Korpman

[11] Patent Number: 4,941,933

[45] Date of Patent: Jul. 17, 1990

[54] METHOD OF MAKING A BODY MEMBER CONFORMABLE DISPOSABLE ARTICLES

[75] Inventor: Ralf Korpman, Bridgewater, N.J.

[73] Assignee: Johnson & Johnson, New Brunswick, N.J.

[21] Appl. No.: 269,275

[22] Filed: Nov. 9, 1988

Related U.S. Application Data

[60] Continuation of Ser. No. 926,601, Nov. 3, 1983, abandoned, Division of Ser. No. 838,440, Mar. 10, 1986, Pat. No. 4,662,874.

[51] Int. Cl.⁵ ............................................. B32B 31/20
[52] U.S. Cl. ............................ 156/160; 112/121.26; 156/221; 156/229; 604/385.1
[58] Field of Search ............... 156/163, 164, 204, 216, 156/221, 222, 223, 227, 229, 160; 604/365, 366, 370, 373, 324, 385.1; 112/121.26, 121.27

[56] References Cited

U.S. PATENT DOCUMENTS

| 2,122,251 | 6/1938 | Hartmann. | |
| 3,730,798 | 5/1973 | Franz. | |
| 3,886,941 | 6/1975 | Duane | 128/287 |
| 3,898,117 | 8/1975 | Taylor | 156/163 |
| 4,036,233 | 7/1977 | Kozak | 128/287 |
| 4,166,464 | 9/1979 | Korpman | 128/287 |

Primary Examiner—Merrell C. Cashion, Jr.
Attorney, Agent, or Firm—Lawrence D. Schuler

[57] ABSTRACT

Body member conformable disposable articles and processes for their preparation are described. A preferred embodiment is a disposable absorbent article comprising a flexible, elastic, moisture impermeable backing film, an absorbent layer superposed thereon and a moisture permeable topsheet joined to the backing film along the edges of the topsheet. A portion of at least one longitudinal edge of the backing film has been folded upon itself and heat sealed together at the fold so that when the backing film is laid flat the aforementioned longitudinal edge will be in stretched condition, thus conferring body member conformability to the article.

9 Claims, 3 Drawing Sheets

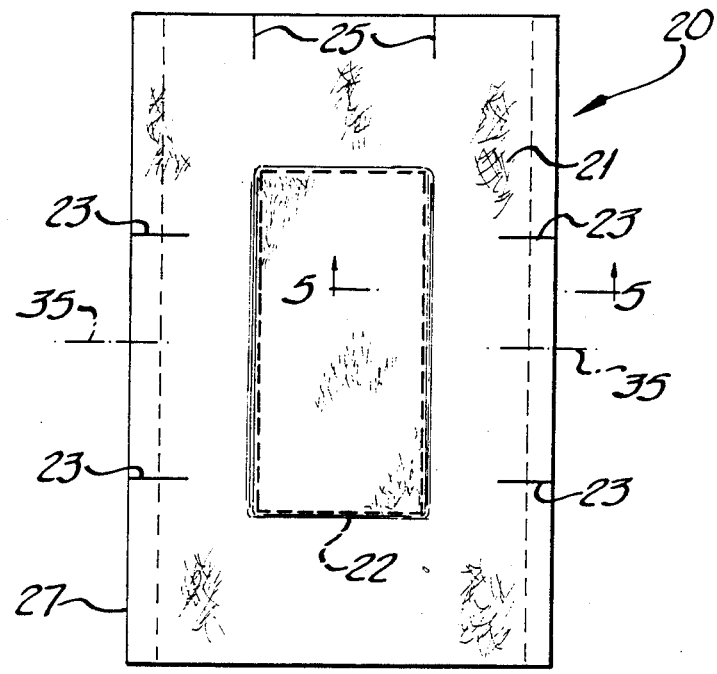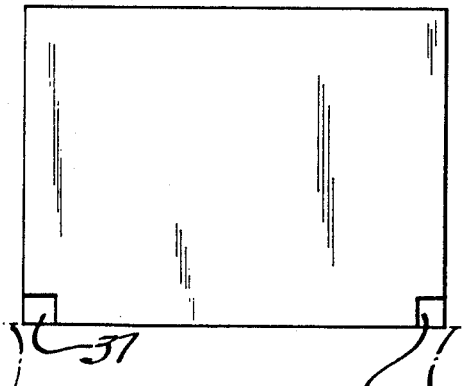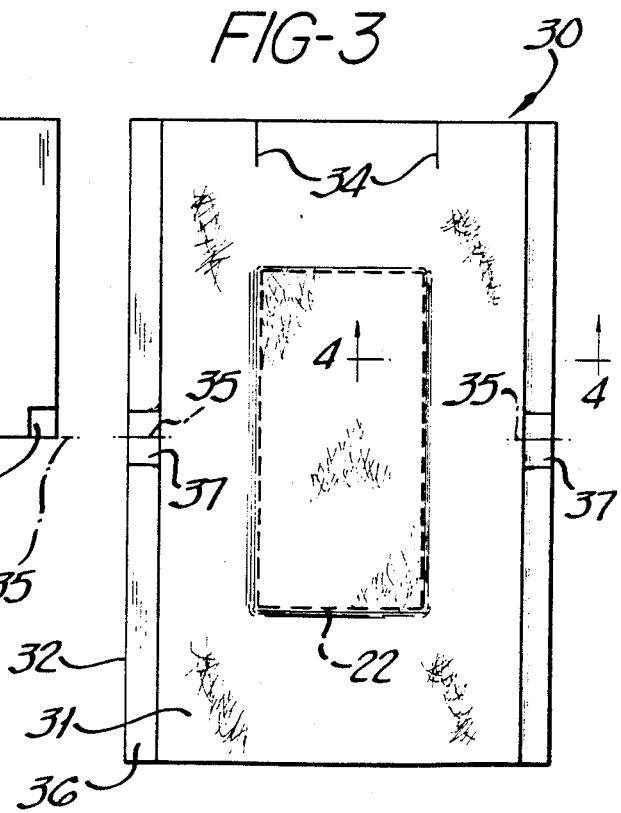

METHOD OF MAKING A BODY MEMBER CONFORMABLE DISPOSABLE ARTICLES

This is a continuation of application Ser. No. 926,601, filed Nov. 3, 1986, now abandoned, which is a division of Ser. No. 838,440, filed Mar. 10 1986, now U.S. Pat. No. 4,662,874.

The present invention relates to body member conformable disposable articles, especially disposable absorbent articles such as diapers and incontinence pads, and processes for their preparation.

BACKGROUND OF THE INVENTION

In recent years the demand for disposable absorbent articles, such as disposable diapers has been increasing. It is important that these diapers should achieve conformability to a body member. Disposable diapers generally are provided with a liquid impermeable backing film, an absorbent layer superposed on the backing film and a liquid permeable topsheet. Diapers are normally fitted to the wearer from a flat state as a result of which they are not completely effective since gaps may develop in the area around the legs through which fluid leaks. In order to overcome this disadvantage, many diapers are now provided with elastic leg stretch components. These stretch components normally comprise elastic bands which are applied to the backing film of the diaper using a hot melt adhesive. The elastic bands are normally applied to the film under stretch and as soon as the hot melt adhesive cools and solidifies, the elastic band relaxes to the original shape, thus pulling the film with it and corrugating the film. This method is expensive and requires a great deal of care to obtain an efficient and proper stretch. Other prior art attempts to overcome the problem of leakage include providing an absorbent layer with an hourglass-like shape or sealing an elastic band between the backing film and the topsheet along the longitudinal edge while in stretch condition for some conformance around the legs. The former approach is accompanied by a reduction in the amount of absorbent material in a critical area and further does not completely avoid gap formation. The latter approach, although decreasing gap formation, has tended to produce a less comfortable product especially if the wearer is an infant. The sealing of an elastic band to the topsheet and backing film may be carried out by the application of adhesive to the band or to both backing film and topsheet. This method of anchoring the rubber band is a cumbersome procedure and moreover tends to produce a harsh feeling on the surface contacting the wearer's skin.

Applicant's copending application Ser. No. 286,441 filed July 24, 1981, now abandoned, overcomes the latter disadvantage in that it consists of applying an elastic pressure-sensitive adhesive tape on the outside of the backing film so that there is no adverse feeling on the surface contacting the wearer's skin.

Prior art disposable diapers have also suffered from the disadvantage of being somewhat unyielding and paper-like and incapable of stretching to any extent, i.e., they lacked elasticity and conformability to the body members to which they are applied. U.S. Pat. No. 4,166,464 overcomes the problem of conformability to the body members, by disclosing a diaper having a thin flexible elastic and easily stretchable thermoplastic backing film as well as a liquid permeable topsheet which is extensible or stretchable such as certain nonwoven fabrics. However, even though the backing film is elastic, that portion of the edge of the backing film adapted to be wrapped around a body member does not necessarily conform completely to the shape of the body member so that a certain amount of leakage of fluid may still occur. This problem is overcome in accordance with the present invention, by providing an elastic backing film in which at least one edge of the backing film is so treated so as to provide a shorter elastic side on the diaper, acting as though it contains a separate elastic band. Thus, in accordance with the present invention there is provided a less cumbersome and a less expensive manner of preparing a "stretch" diaper.

SUMMARY OF THE INVENTION

In accordance with the present invention there is provided a body member conformable disposable article comprising (a) a flexible, elastic and easily stretchable thermoplastic moisture impermeable backing film and (b) an absorbent layer superimposed thereon, at least one portion of at least one edge of said backing film, at a position to be fitted around a body member of the wearer, having been folded upon itself and sealed together at the fold, so that when said backing film is laid flat said one edge thereof is in stretched condition. The disposable article preferably includes a porous facing layer covering the opposite surface of the absorbent layer to that covered by the backing film.

The backing film preferably possesses (1) an elastic recovery from 50% stretch of at least about 75%,
(2) a rubber modulus of not above about 2,000 pounds per square inch at 50% elongation, and
(3) a Gurley stiffness at a thickness of 1 mil of not above about 1.

The topsheet is preferably elastic and easily stretchable. In fact, the elastic film used for the backing film may also be used for the topsheet, in which event said topsheet is suitably shaped or perforated to define a multiplicity of holes or openings through which a liquid may pass into the dressing to be absorbed by the pad. Since the topsheet in this case is nonabsorbent, it also acts as a barrier which protects the wearer or user of the diaper, for instance, from direct contact with the wet pad. Other porous or perforated extensible and elastic topsheets may also be used. In this connection, various types of extensible or stretchable nonwoven fabrics are suitable. The topsheet may be made from an extensible nonwoven fabric which is also elastic such as disclosed in U.S. Pat. No. 3,485,706. A preferred form of this type of nonwoven fabric consists predominately of entangled polyester fibrous elements.

The backing film is most preferably formed from an elastomeric and thermoplastic film-forming composition which comprises an elastomeric component and 0–200 parts of a resin component per 100 parts by weight of the elastomeric component; the elastomeric component consisting essentially of linear or radial A-B-A block copolymers or mixtures of these linear or radial A-B-A copolymers with simple A-B block copolymers, the A-blocks being derived from styrene or styrene homologs and said B-blocks being derived from conjugated dienes or lower alkenes; the resin component consisting essentially of lower molecular weight resins adapted to associate principally with the thermoplastic A-blocks of the block copolymers.

The preferred disposable article of the present invention comprises an integral disposable diaper conformable with a body member comprising (a) a flexible, elastic and easily stretchable thermoplastic moisture impermeable backing film having two longitudinal and two lateral edges, (b) an absorbent layer superposed thereon and (c) a moisture permeable topsheet joined to the backing film along the edges and forming an enclosure for the absorbent layer, at least one portion of at least one longitudinal edge of the backing film, at a position to be fitted around a body member of the wearer, such as the leg, having been folded upon itself and sealed together at the fold, so that when the backing film is laid flat the longitudinal edge thereof is in stretched condition. In the case of a diaper, it is, of course, preferred that at least one portion of each of the two longitudinal edges of the backing film, at positions to be fitted around the two legs of the wearer, have been folded upon themselves and sealed together at the fold so that when the backing film is laid flat, both of the longitudinal edges are in stretched condition.

A preferred embodiment of the diaper of the present invention is one in which the backing film overlaps and extends beyond the topsheet along each longitudinal edge.

A further embodiment of the diaper of the present invention is provided with the topsheet having two longitudinal edges overlaying the corresponding longitudinal edges of the backing film, the topsheet being formed with at least one slit at each longitudinal edge to enhance stretching in the area of the longitudinal edges along the length thereof.

The present invention also comprises an article which includes a fabric layer affixed to the backing film on the side thereof opposite to the side attached to the absorbent layer. This fabric layer provides greater softness to the touch than does the thermoplastic backing film. In the event that the two longitudinal edges of the fabric layer should overlay the corresponding longitudinal edges of the backing film, then the fabric layer is formed with at least one slit at each longitudinal edge to enhance stretching in the area of the longitudinal edges of the fabric layer along the length thereof. More than one slit would be preferred in this connection.

In an embodiment of the present invention in which the topsheet has at least one lateral edge overlaying the corresponding lateral edge of the backing film, the lateral edge of the topsheet is preferably formed with at least one slit (and more preferably two or more) to enhance stretching in the area of the lateral edge of the topsheet along the length thereof.

The present invention is also directed to the process for preparing the absorbent article discussed above. In preparing the absorbent article, the backing film is folded upon itself and sealed at least at one portion of the folded edge of the backing film at the fold. The absorbent layer may be affixed to the backing film before or after the heat sealing step. In order to prepare an article containing only the backing film and an absorbent layer, the latter may be affixed to the backing film with a suitable adhesive or by heat sealing. When the disposable article is intended to be used as a diaper, the absorbent layer will normally be of considerably smaller area than the backing film, but when preparing articles such as gowns and bibs, the absorbent layer may be of substantially the same area as the backing film.

When preparing a diaper which comprises a backing film, an absorbent layer, and a moisture permeable topsheet, wherein the length of the lateral edges of the topsheet are less than those of the corresponding lateral edges of the backing film such that the backing film overlaps and extends beyond the topsheet along each longitudinal edge, the diaper may be prepared by sandwiching the absorbent layer between the backing film and the topsheet and joining the topsheet along its edges to the backing film (preferably by heat sealing). Thereafter, at least one portion of at least one longitudinal edge of the backing film is folded upon itself and said one portion of the folded edge of the backing film is sealed at the fold (preferably by heat sealing, although a suitable adhesive may be used). It is of course preferable, in the case of a diaper to fold at least one portion of each of the two longitudinal edges of the backing film upon themselves and to thereafter seal said portions of the folded edges of the backing film at the folds. Although only one folded and sealed portion (which will hereinafter be referred to as "pinched portion") is necessary at each longitudinal edge of the diaper, nevertheless it may be desirable to prepare two or more of such pinched portions along each longitudinal edge in order to reduce the length thereof and thus to increase the effective stretch. The pinched portions may be spaced apart from one another or alternatively a portion of each longitudinal edge may be corrugated with a number of overlapping folds and the corrugated portion thereafter sealed together.

The heat sealing step, per se, is carried out in a conventional manner. However, Applicant has found it expedient to place each corner of the folded over edge of the backing film between the nips of a pair of heated rollers in order to effect the heat sealing of such pinched portions of the disposable article.

In the instance wherein the topsheet has substantially the same area as the backing film (that is when the longitudinal edges of the topsheet overlay the corresponding longitudinal edges of the backing film) it is desirable to form the topsheet with at least one slit in each longitudinal edge thereof to enhance stretching in the area of the longitudinal edges of the topsheet along the length thereof. In the above instance, it is preferable to first prepare the sealed "pinched portions" of the longitudinal edges of the backing film and to sandwich the absorbent layer between the backing film and the topsheet; whereafter the topsheet is joined to the backing film along the edges of the topsheet (preferably by heat sealing in a conventional manner).

In an alternative embodiment, in the instance wherein the topsheet has substantially the same area as the backing film, at least one notch may be formed in the topsheet in the area wherein the "pinched portion" of the longitudinal edge of the backing film is to be formed. In this case the "pinching" may be carried out before or after the absorbent layer is sandwiched between the backing film and the topsheet.

The backing film of the present invention must, of course, be elastic and easily stretchable as well as highly flexible. Furthermore, it is also highly advantageous if the backing film is highly thermoplastic and easily heat sealable. Any backing film having the aforementioned characteristics would be suitable for the present invention. However, it is preferred that the backing film should possess an elastic recovery from 50% stretch of at least about 75%, preferably at least about 90%; a 50% rubber modulus of not above about 2,000, preferably not above about 1,000 pounds per square inch at 50% elongation and a Gurley stiffness of not above about 1 at a thickness of about 1 mil. This is a highly flexible easily stretchable film which is elastic and tends to return to its original configuration when in a diaper and stretched around a baby for example. However, since the film has a low modulus and stretches easily it will not grip the baby too tightly either during stretching or after it is secured in position. The edges of the diaper having the "pinched portions" of the present invention convert the diaper into a "stretch" diaper, i.e., the kind of diaper having elastic bands, or the equivalent, which render the diaper conformable around body members such as the legs.

As pointed out above, the backing film of the present invention is preferably highly thermoplastic and easily heat sealable, i.e., it is adapted to form permanent heat seals to substrates such as paper and boxboard at relatively low heat sealing peak temperatures, generally not above about 350° F., in less than 4 seconds of clamping time, as described more fully hereinafter. It also preferably is capable of high elongation before breaking, i.e., it possesses an elongation to break of at least about 300 percent, preferably at least about 400 percent.

The preferred film of this invention is formed from an elastomeric and thermoplastic film-forming composition which comprises an elastomeric component and 0–200 parts, preferably 85–200 parts of a resin component per one hundred parts by weight of the elastomeric component. The elastomeric component consists essentially of linear or radial A-B-A block copolymers or mixtures of these linear or radial A-B-A block copolymers with simple A-B block copolymers. In these block copolymers the A-blocks are derived from styrene or styrene homologs and the B-blocks are derived from conjugated dienes or lower alkenes. The resin component consists essentially of low molecular weight resins, preferably having a number average molecular weight not above about 3,000, and which are adapted to associate principally with the thermoplastic A-blocks of the said block copolymers.

In addition, the thermoplastic-elastomeric composition used for preparing the backing film may be of a novel alloy such as that of an A-B-A block copolymer and a copolyester, e.g., an ester polymer of at least two different ester units as more fully described in U.S. Pat. No. 4,301,255.

The above backing film may be extruded hot from particulate, solid or liquid film-forming components, cast from a hot melt, formed by coating from solution, or the like. It preferably is extruded from dry particles. The film then is laminated with a layer of absorbent material which may comprise paper, wood pulp or other absorbent material such as superabsorbents in a suitable matrix and preferably is configured so as to be extensible, such as by creping. In one preferred form of the invention, the backing film is heat sealed to the absorbent layer by using the high sealing properties of the backing film itself. The heat seals may be formed only at the corners of the dressing or otherwise spaced from one another for increased flexibility. In disposable diapers, the side of the absorbent layer opposite to the backing normally is covered with a highly porous facing sheet of paper or nonwoven fabric.

In another preferred form of the article of this invention, the backing film and the absorbent layer or pad are assembled in such a way that portions of the backing film are extensible independently of the absorbent layer in the direction of their interface. Thus, these portions can be stretched without stretching the absorbent pad so that the pad need not be extensible. For instance, the backing film may extend beyond the edges of the absorbent pad to form flaps on either side of the dressing which are extensible independently of the absorbent pad or that portion of the backing which is directly attached to the pad, or the absorbent pad may be attached to the backing over only a limited region disposed inwardly of corners of the pad to permit those portions of the backing film superimposed with marginal portions of the pad to be stretched or extended independently of those marginal portions, as disclosed in U.S. Pat. No. 3,981,306. Furthermore, in disposable diapers the shape of the backing film and the shape of the absorbent pad, the relationship between the backing film and the pad, and the attachment or adherence between the film and the pad all may be varied to provide different extensibility and conformability characteristics.

In still a different embodiment of the article of this invention the elastic and easily stretchable film material of the backing also may be used for the topsheet or facing film which covers the opposite surface of the absorbent layer or pad. The elastic topsheet is suitably shaped or perforated to define a multiplicity of holes or openings through which liquid may pass into the dressing to be absorbed by the pad. Since the topsheet in this case is nonabsorbent, it also acts as a barrier which protects the wearer or user of a diaper, for instance, from direct contact with the wet pad. This form of the article of this invention is particularly conformable since both the backing film and the topsheet are flexible, elastic and easily stretchable. Other porous or perforated extensible and elastic topsheets also may be used in the article of this invention. As indicated hereinbefore, various types of extensible or stretchable nonwoven fabrics may be used as topsheets. In one preferred embodiment of a disposable diaper according to this invention the topsheet is an extensible nonwoven fabric which also is elastic.

As indicated hereinbefore, the film-forming composition useful for this invention may comprise an elastomeric component and a resin component, and the elastomeric component may consist essentially of linear or radial A-B-A block copolymers or mixtures of these A-B-A block copolymers with simple A-B block copolymers. However, the proportion of A-B block copolymers in the mixture of A-B-A and A-B block copolymers should not exceed about 75% by weight and lower percentages normally would be used.

The A-B-A block copolymers are of the type which consist of A-blocks (end blocks) derived, i.e., polymerized or copolymerized, from styrene or styrene homologs; and B-blocks (center blocks) derived from conjugated dienes, such as isoprene or butadiene, or from lower alkenes, such as ethylene and butylene. Small proportions of other monomers also may enter into the block copolymers themselves. The individual A-blocks have a number average molecular weight of at least about 6,000, preferably in the range of about 8,000–30,000, and the A-blocks constitute about 5–50 percent, preferably about 10–30 percent, by weight of the block copolymer. The number average molecular weight of the B-blocks for linear A-B-A block copolymers preferably is in the range of about 45,000–180,000 and that of the linear copolymer, itself, preferably is in the range of about 75,000–200,000. The number average molecular weight of the radial A-B-A copolymers preferably is in the range of about 125,000-400,000. The designation A-B-A includes what are sometimes called A-B-C block copolymers wherein the end blocks are different from one another but both are derived from styrene or styrene homologs. This applies both to linear and radial block copolymers. The term "linear block copolymer" (or copolymers) includes branched A-B-A copolymers as well as unbranched A-B-A copolymers.

The radial A-B-A polymers useful in this invention are of the type described in U.S. Pat. No. 3,281,383 and conform to the following general formula: $(A-B)_nX$, wherein A is a thermoplastic block polymerized from styrene or styrene homologs, B is an elastomeric block derived from conjugated dienes or lower alkenes, as indicated above, X is an organic or inorganic connecting molecule with a functionality of 2-4 as described in U.S. Pat. No. 3,281,383 or possibly with a higher functionality as described in the article entitled "New Rubber is Backed by Stars" appearing on page 35 of the June 11, 1975 issue of *Chemical Week*. "n" then is a number corresponding to the functionality of X.

The A-B block copolymers useful for this invention are of the type described in U.S. Pat. Nos. 3,519,585 and 3,787,531 and comprise A and B-blocks derived from the monomers described hereinbefore in connection with the A-B-A copolymers.

The elastomeric component of the film-forming composition useful for this invention may include small amounts of other more conventional elastomers but these should not exceed about 25 percent by weight of the elastomeric component. These other elastomers may include, highly broken down natural rubbers and butadiene-styrene random copolymer rubbers, synthetic polyisoprene, chloroprene rubbers, nitrile rubbers, butyl rubbers, and the like. Potentially elastomeric liquid polymers also may be employed as additives but normally in lower proportions not above about 10 percent by weight of the elastomeric component.

The resin component useful for the backing film of this invention, if employed, consists essentially of low molecular weight resins which are adapted to associate principally with, and are principally compatible with, the thermoplastic A-blocks of the said block copolymers. These include low molecular weight resins based on poly-alpha-methylstyrene, polystyrene, polyvinyl toluene and similar aromatic resins, as well as copolymers thereof, coumarone indene and related cyclic compounds. Preferred resins for this purpose possess a number average molecular weight not above about 3,000 although higher molecular weight resins in the low molecular weight range also may be employed. Small proportions, i.e., not above about 25 percent of the elastomeric component, of various other resins, which (if tack is desired) may include conventional tackifying resins such as hydrocarbon resins, rosin, hydrogenated rosin, rosin esters, polyterpene resins, and the like, also may be employed in the resin component of the film-forming composition.

The film-forming composition also may contain relatively small proportions of various other materials such as antioxidants, heat stabilizers and ultraviolet absorbers, release agents, extenders, fillers and the like. Typical antioxidants are 2,5 ditertiary amyl hydroquinone and ditertiary butyl cresol. Similarly, conventional heat stabilizers such as the zinc salts of alkyl dithiocarbamates may be used. Lecithin is one release material which has been found to be particularly suitable in minor amounts in this type of extrudable particulate mixture. However, waxes and various other release agents or slip agents also may be added in this manner.

Relatively small proportions, in the neighborhood of 25 parts by weight of the elastomeric component, of various extenders such as higher molecular weight polystyrenes, nonreactive phenol-formaldehyde resins, linear polyester resins, polyethylene, polypropylene, etc., also may be included in the film-forming composition. Similarly, the particulate mixture may include relatively small proportions, say 25 parts by weight of the elastomeric component, of fillers and pigments such as zinc oxide, aluminum hydrate, clay calcium carbonate, titanium dioxide, carbon black and others. Many of these fillers and pigments also may be used in powdered form as parting agents to be mixed with thermoplastic elastomer particles to prevent these particles from agglomerating prior to blending with resin particles and other materials.

BRIEF DESCRIPTION OF THE DRAWINGS

FIG. 1 is a view of the topsheet side of a rectangular diaper while retained in a flat position. This view shows an absorbent pad sandwiched between an elastic thermoplastic moisture impermeable backing film and a porous topsheet.

FIG. 2 is a view of the backing film of FIG. 3 folded upon itself, in the middle, a section of each of the two longitudinal edges of the backing film having been sealed together at the fold.

FIG. 3 is a top view of the backing film shown in FIG. 2 after the latter has been unfolded and placed in a flat position and showing the "pinched" sealed sections in each longitudinal edge of the backing film, whereby each of said longitudinal edges is in a stretched state.

DETAILED DESCRIPTION OF THE INVENTION

Figure 5:
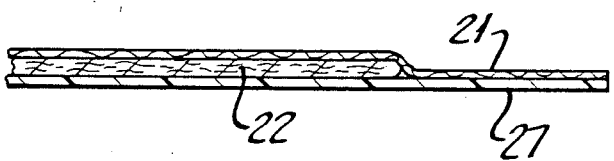
FIG. 5 is a sectional view taken along 5—5 of FIG. 1.
Figure 7:
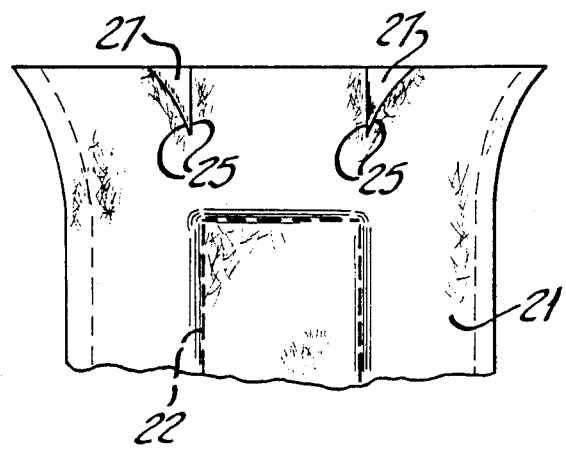
FIG. 7 is a top view of the topsheet side of the diaper of FIG. 1, showing the manner in which slits formed in the upper lateral edge of the diaper, have opened up after the upper edge is stretched such as in the instance when said upper edge is pulled tight around a baby's waist.

Referring first to FIG. 1 there is shown a flat view of an integral disposable diaper 20 having a fluid permeable topsheet 21, an absorbent layer 22 shown with dashed lines and a fluid impermeable backing film 27, the absorbent layer 22 being sandwiched between said topsheet 21 and said backing film 27. The laminated structure of these three components is more clearly shown in FIG. 5. It will be noted that in FIG. 1 the topsheet 21 completely overlays the backing film 27. Slits 23 and 25 are formed in the topsheet 21, so that when the diaper is stretched, the slits 21 and 25 enhance the ability of the edges of the topsheet 21 to stretch accordingly. In this connection, reference should be made to FIG. 7 which shows the diaper when it is stretched laterally at the top edge such as would be the case when a baby is diapered and the diaper is pulled tight around the baby's waist so that the slits 25 will tend to open up and the backing film 27 may be seen through the openings.

Figure 4:
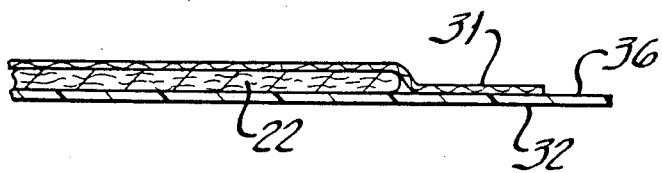
FIG. 4 is a sectional view taken along 4—4 of FIG. 3.

In FIG. 3 there is shown a flat view of an integral disposable diaper 30 having a fluid permeable topsheet 31, an absorbent layer 22 shown with dashed lines and a fluid impermeable backing film 32, the absorbent layer 22 being sandwiched between said topsheet 31 and said backing film 32. The laminated structure of these three components is more clearly shown in FIG. 4. In said FIG. 4 it will be noted that the topsheet 31 extends over a smaller area than the backing film 32 (i.e., the backing film 32 overlaps and extends beyond the topsheet 31 along each longitudinal edge 36). In view of said overlapping edge 36 in diaper 30 of FIG. 3, it is not essential to provide any slits in the longitudinal edges of the topsheet 31 of the embodiment of FIG. 3 (such as the slits 23 in the topsheet 26 of the embodiment of FIG. 1). However, slits 34 are formed in the lateral edge of the diaper 30 as shown in FIG. 3, so that when the latter is stretched at the top edge the slits 34 enhance the ability of the topsheet 31 to stretch.

Turning to FIG. 2 it will be seen that the backing film 32 has been folded midway upon itself around the midline 35 and the corner portions 37 have been sealed (preferably by means of heat, although an adhesive may be used instead). The heat sealing is preferably carried out by passing each corner portion 37 of the folded backing film 32, between the nips of pairs of heated rollers at temperatures in the range between 250° and 350° F. A further embodiment of the present invention comprises corrugating the portions 37 of the folded backing film 32 before the heat sealing step is carried out.

It is desirable that the sealed "pinched portions" 37 be equal in length along the longitudinal edges of the diaper so that the reduction in length of said longitudinal edges should be of equal magnitude. After the backing film 32 is opened up, and laid flat as shown in FIG. 3, the longitudinal edges 36 of the diaper will be under stretch. If desired, backing film 32 could be folded, a further time, around a line remote from midline 35 and then sealed at the new fold. In this manner, two or more "pinched portions" can be sealed and formed in each longitudinal edge of the diaper so as to proportionately increase the amount of stretch therein.

The absorbent layer 22 and the topsheet 31 may be affixed, in a conventional manner, to the backing film 32 before or after the preparation of the "pinched portions" 37 when preparing diaper 30 as shown in FIG. 3. When preparing diaper 20 as shown in FIG. 1, it is more expedient to first prepare the "pinched portions" in the longitudinal edges of the backing film 27 and thereafter to sandwich the absorbent layer 22 between the backing film 27 and the topsheet 21 and joining the topsheet 21, along its edges to the backing film using a suitable adhesive or by heat sealing.

Figure 6:
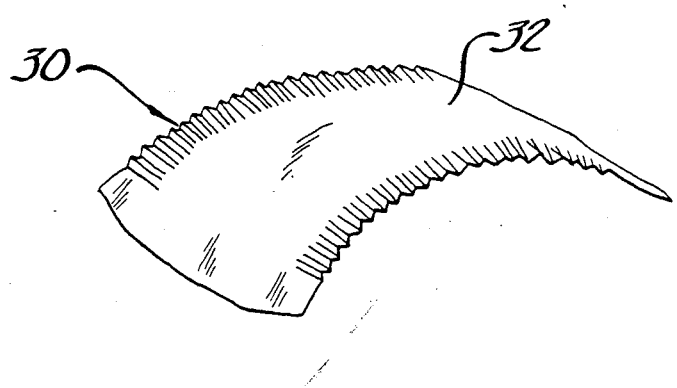
FIG. 6 is a perspective view of the diaper of FIG. 3 after it has been released from its flat position showing puckered portions of the backing film due to the release of the stretching of the "pinched" longitudinal edges.

As will be noted from FIG. 6, when the diaper of FIG. 3 is no longer held flat, the stretch in the longitudinal edges will cause the diaper to be curved as in any normal "stretch" diaper and the backing film 32 will become slightly puckered along the longitudinal edges.

Figure 8:
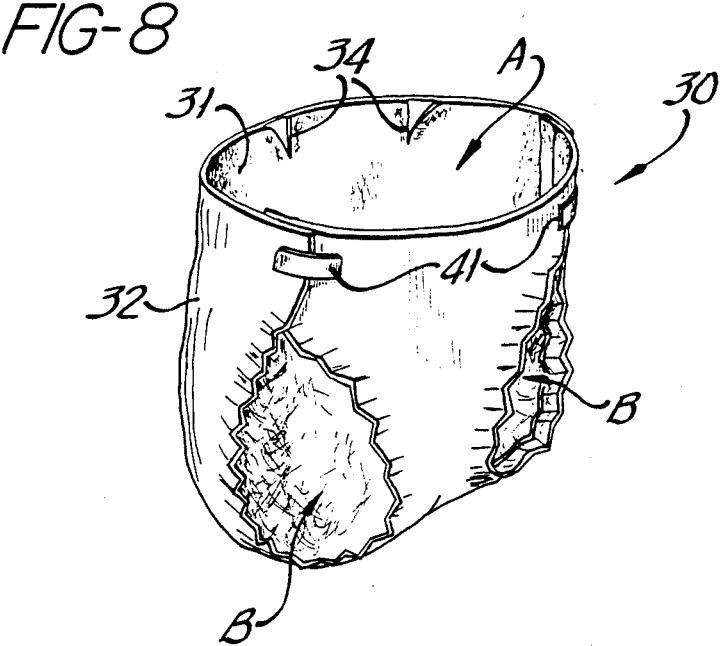
FIG. 8 is a perspective view of the diaper of FIG. 3 in its configuration as applied to an infant.

FIG. 8 shows the diaper of FIG. 3 in its configuration as applied to an infant whose trunk would occupy space "A" and the leg spaces "B". Conventional fastening tabs 41 may be employed to hold the diaper in place around the trunk. Due to the stretch around the infant's waist, the slits 34 are shown to have been opened up. The longitudinal edges of the backing film 32 form a tight fit around the leg spaces "B".

U.S. Pat. No. 4,036,233 discloses a disposable diaper having a topsheet and a backsheet, one of which is stretchable, the other nonstretchable and wherein both extend beyond the edges of the absorbent material to provide a waistband. The nonstretchable sheet is provided with openings to permit stretching of the waistband. These openings have a somewhat similar effect to the slits 25 shown in FIG. 7 of the present invention.

The following examples of the backing films useful in absorbent articles according to this invention are given only by way of illustration and are not intended to limit the scope of the invention in any way. Table A gives the film compositions for Examples I–III together with the physical characteristics of the films. In the examples, all proportions are expressed in parts per one hundred parts by weight of the total elastomeric component unless otherwise indicated.

Film thickness is expressed in mils, or thousandths of an inch, tensile strength is pounds per square inch to break the film as measured on an Instron tensile tester with an initial jaw separation of one inch at a speed of twelve inches per minute, and elongation is the percentage which the film must be stretched in a given direction to break it, i.e., stretched dimension at break minus normal dimension, over normal dimension in that direction, times a hundred. In all cases the designation "M.D." means "machine direction" lengthwise in the direction of processing and "C.D." means "cross direction."

Elastic recovery is percentage of immediate recovery in length after being stretched fifty percent of original length and then released to allow free return. It is a function of the amount of stretch recovered over the amount of stretch. The amount of stretch equals the length when stretched minus the original length and the amount of stretch recovered equals the length when stretched minus the length after recovery. Rubber modulus is tensile stress in pounds per square inch of initial cross section measured at one half inch extension per inch of length or 50 percent elongation. This also is called 50 percent rubber modulus.

Gurley stiffness is measured as an opposite or inverse measure of flexibility with a standard Gurley stiffness tester using 1.0 by 1.5 inch samples with ¼ inch of sample in the jaw and ¼ inch overlapping the blade. The measured Gurley stiffness then is converted to stiffness at a thickness of one mil by dividing the measured stiffness by the cube of the measured thickness in mils. The coefficient of sliding friction is measured by drawing the film samples horizontally over a chrome plated smooth metal panel with a 500 gram weight on top of the film. This is done in a TLMI adhesion tester at a pulling speed of 12 inches per minute.

Heat sealability is measured by clamping each film sample in an open sandwich with a sheet of standard fiberboard test material between the jaws of an Erich International Corporation Bag Sealer at 42 p.s.i. air pressure. The fiberboard is Standard Reference Material 1810 specified in United States Department of Commerce Standard for Tape Adhesion Testing No. 16 (M:L-B-131E, Class 2). One of the jaws is heated and the other is unheated. The boxboard is placed in contact with the heated jaw and the film in contact with the unheated jaw. Both jaws are cooled to ambient temperature by air jets prior to clamping. When the test material is in position between the jaws, the bottom jaw is heated by an electric heater to seal the film to the boxboard by heat transferred through the board. The heating time period required to heat the lower jaw to the minimum peak temperature necessary to permanently heat seal the film of the boxboard, using a clamping period of 4 seconds, then is measured. The minimum peak permanent heat sealing temperature corresponding to the time recorded, then is obtained by reference to a time-temperature calibration curve for the instrument obtained by measuring temperatures at the bonding surface of the boxboard. The minimum peak temperature referred to is that reached at the time the electric heater is deenergized at the end of the heating time period.

TABLE A

| Ingredients & Characteristics | Examples | | |
|---|---|---|---|
| | I | II | III |
| Kraton 1107 S-I-S Linear Copolymer | 100 | | 100 |
| Solprene 420 S-I-S Radial Copolymer | | 100 | |
| Amoco 18-210 Resin | | | 150 |
| Amoco 18-290 Resin | 100 | 100 | |
| Zinc Dibutyl Dithiocarbamate (Antioxidant) | 1 | 2 | 1 |
| 2,5 Ditertiary Amyl Hydroquinone (Antioxidant) | ½ | ½ | ½ |
| Titanium Dioxide Pigment | 5 | | |
| Thickness, (Mils) | 3.6 | 4.2 | 3.0 |
| Rubber modulus @ 50% Elongation, lbs./in.$^2$ | 800 | 115 | 475 |
| Elongation (M.D.),% | 530 | 1200 | 2100 |
| Elongation (C.D.),% | 750 | 1140 | 1260 |
| Tensile Strength (M.D.), lbs./in.$^2$ | 1220 | 600 | 900 |
| Tensile Strength (C.D.), lbs./in.$^2$ | 1050 | 570 | 970 |
| Gurley Stiffness, mg./in.$^2$/ mil | 0.38 | 0.42 | 0.05 |
| Heat Sealing Temperature, °F. | 250 | 240 | 250 |
| Friction Coefficient (Dynamic) | 2.58 | 2.60 | 2.23 |
| % Elastic Recovery After 50% Elongation | 98 | 95 | 95 |

It will be seen that the films of all of the above examples are highly elastic, i.e., possess an elastic recovery after 50 percent elongation of well above about 90 percent. Furthermore, all the films possess a low rubber modulus, in these examples, not above about 1,000 lbs./in.$^2$ at 50 percent elongation.

The films of the examples are not particularly oriented as evidenced from the tensile strength readings in the machine and cross-directions and generally possess a high elongation, i.e., at least about 500 percent in both directions.

The films are highly flexible, exhibiting Gurley stiffness readings as low as 0.05 mg./in.$^2$/mil and no higher than 0.42 mg./in.$^2$/mil. They also are not slippery, i.e., they possess a dynamic coefficient of friction well above 0.5, more specifically between 2 and 3. The maximum permanent heat sealing temperature determined as described hereinbefore is about 250° F., well below 350° F.

In the foregoing examples Kraton 1107 copolymer is a thermoplastic elastomeric A-B-A (styrene-isoprene-styrene) block copolymer offered by the Shell Chemical Company, wherein the styrene content (that of the A-blocks) is about 12-15 percent, closer to 15 percent by weight of the block copolymer, and the polymer possesses a solution viscosity of about 2,000 centipoises at 25 percent solids in toluene at room temperature (using a Brookfield Viscometer with a No. 4 spindle at 60 r.p.m.), and a number average molecular weight of about 110,000-125,000. Solprene 420 copolymer is a radial styrene-isoprene-styrene block copolymer of the type described hereinbefore which has a number average molecular weight of 240,000 and a styrene content of about 15 percent.

Amco 18-210 and 18-290 resins are solid polyalphamethyl styrenes offered by Amoco Chemical Co., with softening points of about 210° F. (99° C.) and 290° F. (143° C.) respectively.

Although the present invention has been described in detail with respect to diapers where there is a special need, it is obvious that it may be adapted to any article of similar nature in which conformability is desired, particularly conformability around a body member such as neck, wrist, ankle, waist, etc. Thus it is adaptable to be employed with disposable gowns, athletic tape, bibs, surgical stockinettes, bandages and other health care products and industrial products.

In contrast to diapers and incontinence pads, other articles may comprise a backing film and an absorbent sheet. A gown or other article may be made partly of a nonabsorbent moisture impermeable material similar to a backing film of a diaper. These articles may be made selectively conformable according to the method of the present invention by forming a sealed "pinched" portion in the longitudinal edges thereof at the desired positions. In articles other than diapers and incontinence pads, the source of moisture is generally external so that a topsheet is not necessary to protect the skin from the liquid filled absorbent pad as is necessary in a diaper.

Having now described the diaper in specific detail and exemplified the manner in which it may be carried into practice it will be readily apparent to those skilled in the art that innumerable variations, applications, modifications and extensions of the basic principles involved may be made without departing from its spirit or scope.

I claim:

1. A process for preparing a body member conformable disposable article comprising: p1 (a) an electric thermoplastic moisture impermeable backing film, and
   (b) an absorbent layer superposed thereon, at least one portion of at least one edge of said backing film, at a position to be fitted around a body member of the wearer, having been folded upon itself and sealed together at the fold, so that when said backing film is laid flat said one edge thereof is in stretched condition; which process comprises providing an elastic thermoplastic moisture impermeable backing film, folding at least one portion of at least one edge of said backing film upon itself around a fold line running transversely of said one edge and forming at least one pinched portion at the fold by sealed a portion of the folded edge of said backing film together at the fold, providing an absorbent layer, and affixing the absorbent layer to the backing film.

2. A process according to claim 1, in which the absorbent layer is affixed to the backing film before the step of sealing the portion of the folded edge thereof.

3. A process according to claim 1, in which the absorbent layer is affixed to the backing film after the step of sealing the portion of the folded edge thereof.

4. A process according to claim 1, wherein the backing film prossesses:
   1. an electric recovery from 50 percent stretch of at least about 75 percent.

2. a rubber modulus of not about 2,000 pounds per square inch at 50 percent elongation, and
3. a Gurley stiffness at a thickness of 1 mil of not above about one.

5. A process for preparing an integral disposable diaper conformable with a body member comprising:
   (a) an elastic thermoplastic moisture impermeable backing film having two longitudinal and two lateral edges,
   (b) an absorbent layer superposed thereon, and
   (c) a moisture permeable topsheet joined to said backing film along the edges of the topsheet and forming an enclosure for said absorbent layer, at least one portion of at least one longitudinal edge of said backing film, at a position to be fitted around a body member of the wearer, having been folded upon itself and heat sealed together at the fold so that when said backing film is laid flat, said one longitudinal edge thereof is in stretched condition; which process comprises providing an elastic thermoplastic moisture impermeable backing film having two longitudinal and two lateral edges, providing an absorbent layer, providing a moisture permeable topsheet having two longitudinal and two lateral edges, the lengths of the lateral edges of the topsheet being less than those of the corresponding lateral edges of the backing film, sandwiching the absorbent layer between the backing film and the topsheet whereby the backing film overlaps and extends beyond the topsheet along each longitudinal edge, joining the topsheet along its edges to the backing film, folding at least one portion of at least one longitudinal edge of said backing film upon itself around a fold line running transversely of said longitudinal edge and forming at least one pinched portion at the fold by heat sealing a portion of the folded edge of said backing film together at the fold, 6. A process for preparing an integral disposable diaper conformable with a body member comprising:
   (a) an elastic thermoplastic moisture impermeable backing film having two longitudinal and two lateral edges,
   (b) an absorbent layer superposed thereon, and
   (c) a moisture permeable topsheet joined to said backing film along the edges of the topsheet and forming an enclosure for said absorbent layer, at least one portion of at least one longitudinal edge of said backing film, at a position to be fitted around a body member of the wearer, having been folded upon itself and heat sealed together at the fold so that when said backing film is laid flat, said one longitudinal edge thereof is in stretched condition, said topsheet having two longitudinal edges overlaying the corresponding longitudinal edges of said backing film, said topsheet being formed with at least one slit at each longitudinal edge to enhance stretching in the area of said longitudinal edges of said topsheet along the length thereof; which process comprises providing an elastic thermoplastic moisture impermeable backing film having two longitudinal and two lateral edges, providing an absorbent layer, providing a moisture permeable topsheet having two longitudinal and two lateral edges, forming at least one slit at each longitudinal edge of said topsheet, folding at least one portion of each of said two longitudinal edges of said backing film upon themselves around fold lines running transversely of said longitudinal edges and forming at least one pinched portion at each fold by heat sealing a portion of each folded edge of said backing film together at the folds, and thereafter, sandwiching the absorbent layer between the backing film and the topsheet and joining the topsheet along its edges to the backing film so that the two longitudinal edges of said topsheet overlay the corresponding longitudinal edges of said backing film.

7. A process according to claim 5, wherein the topsheet comprises a nonwoven fabric.

8. A process according to claim 1, which comprises heat sealing the portion of the folded edge.

9. A process according to claim 1, which comprises sealing the portion of the folded edge with an adhesive.

* * * * *

UNITED STATES PATENT AND TRADEMARK OFFICE
CERTIFICATE OF CORRECTION

PATENT NO. : 4,941,933
DATED : July 17, 1990
INVENTOR(S) : Ralf Korpman

It is certified that error appears in the above-identified patent and that said Letters Patent is hereby corrected as shown below:

Claim 1, Column 12, Line 55: "by sealed a portion" should be --by sealing a portion--.

Claim 1, column 12, Line 40: delete "pl".

Claim 1, Column 12, Line 40: "electric" should be --elastic--.

Claim 4, Column 12, Line 67: "electric" should be --elastic--.

Signed and Sealed this

Tenth Day of November, 1992

Attest:

DOUGLAS B. COMER

*Attesting Officer*    Acting Commissioner of Patents and Trademarks